US009241660B2

(12) United States Patent
Walters et al.

(10) Patent No.: US 9,241,660 B2
(45) Date of Patent: Jan. 26, 2016

(54) INSERTION DEVICE AND METHOD

(71) Applicant: Senseonics, Incorporated, Germantown, MD (US)

(72) Inventors: Steven J. Walters, Ellicott City, MD (US); Casey J. O'Connor, Gaithersburg, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

(21) Appl. No.: 13/705,816

(22) Filed: Dec. 5, 2012

(65) Prior Publication Data

US 2013/0313133 A1    Nov. 28, 2013

Related U.S. Application Data

(63) Continuation of application No. 11/447,980, filed on Jun. 7, 2006, now abandoned.

(60) Provisional application No. 60/688,371, filed on Jun. 8, 2005.

(51) Int. Cl.
*A61B 5/00* (2006.01)
*A61B 5/145* (2006.01)
*A61M 37/00* (2006.01)

(52) U.S. Cl.
CPC ......... *A61B 5/14503* (2013.01); *A61B 5/14532* (2013.01); *A61B 5/6849* (2013.01); *A61M 37/0069* (2013.01)

(58) Field of Classification Search
CPC ........... A61B 5/14503; A61B 5/14532; A61B 5/6849; A61M 37/0069

USPC ......... 600/562–572, 309, 414, 420, 426–427, 600/431; 482/79–80; 601/23, 27–28; 606/142, 151, 153, 185, 219
See application file for complete search history.

(56) References Cited

U.S. PATENT DOCUMENTS

| 2,620,796 A | 12/1952 | Eriksen et al. |
| 2,659,369 A | 11/1953 | Lipman |
| 2,883,984 A | 4/1959 | Candido, Jr. et al. |
| 3,025,953 A | 3/1962 | Taggart et al. |
| 3,744,493 A | 7/1973 | Booher et al. |
| 4,213,456 A | 7/1980 | Bottger |

(Continued)

FOREIGN PATENT DOCUMENTS

| EP | 0 564 038 A2 | 10/1993 |
| EP | 1 300 129 A2 | 4/2003 |

(Continued)

*Primary Examiner* — Rene Towa
(74) *Attorney, Agent, or Firm* — Rothwell, Figg, Ernst & Manbeck, P.C.

(57) ABSTRACT

The present invention provides an insertion device and method for implanting a biosensor into a patient subject. In one embodiment, a biosensor is stored in the instrument's hydration chamber which enables the biosensor to maintain proper hydration and sterilization prior to insertion. The instrument further includes a plunger that travels along a channel within the support device. After the biosensor is placed into the channel, the user pushes the plunger causing the biosensor to move through the channel and a hollow tube and into the patient subject. The present invention also provides for packaging and storing a biosensor and insertion device so that the biosensor is hydrated and sterile prior to insertion.

4 Claims, 16 Drawing Sheets

(56) References Cited

U.S. PATENT DOCUMENTS

| | | |
|---|---|---|
| 4,451,254 A | 5/1984 | Dinius et al. |
| 4,661,103 A | 4/1987 | Harman |
| 4,787,384 A | 11/1988 | Campbell et al. |
| 4,871,094 A | 10/1989 | Gall et al. |
| 5,002,548 A | 3/1991 | Campbell et al. |
| 5,074,318 A | 12/1991 | Campbell et al. |
| 5,098,439 A | 3/1992 | Hill et al. |
| 5,281,197 A | 1/1994 | Arias et al. |
| 5,405,324 A | 4/1995 | Wiegerinck |
| RE34,936 E | 5/1995 | Campbell et al. |
| D358,644 S | 5/1995 | Park |
| 5,413,631 A | 5/1995 | Gray et al. |
| 5,468,246 A | 11/1995 | Blake |
| 5,486,183 A | 1/1996 | Middleman et al. |
| 5,558,637 A | 9/1996 | Allonen et al. |
| 5,562,613 A | 10/1996 | Kaldany |
| 5,634,913 A | 6/1997 | Stinger |
| 6,258,056 B1 | 7/2001 | Turley et al. |
| 6,330,464 B1 | 12/2001 | Colvin, Jr. et al. |
| 6,436,068 B1 | 8/2002 | Bardy |
| 6,443,893 B1 | 9/2002 | Schnakenberg et al. |
| 6,497,708 B1 | 12/2002 | Cumming |
| 6,530,895 B1 | 3/2003 | Keirn |
| 6,620,162 B2 | 9/2003 | Kuslich et al. |
| 6,936,006 B2 | 8/2005 | Sabra |
| 2004/0127765 A1 | 7/2004 | Seiler et al. |
| 2004/0230198 A1 | 11/2004 | Manzi et al. |
| 2005/0064046 A1 | 3/2005 | DiTrolio |
| 2005/0148945 A1 | 7/2005 | Chen |

FOREIGN PATENT DOCUMENTS

| | | |
|---|---|---|
| GB | 904 257 | 8/1962 |
| WO | 03/022133 A2 | 3/2003 |

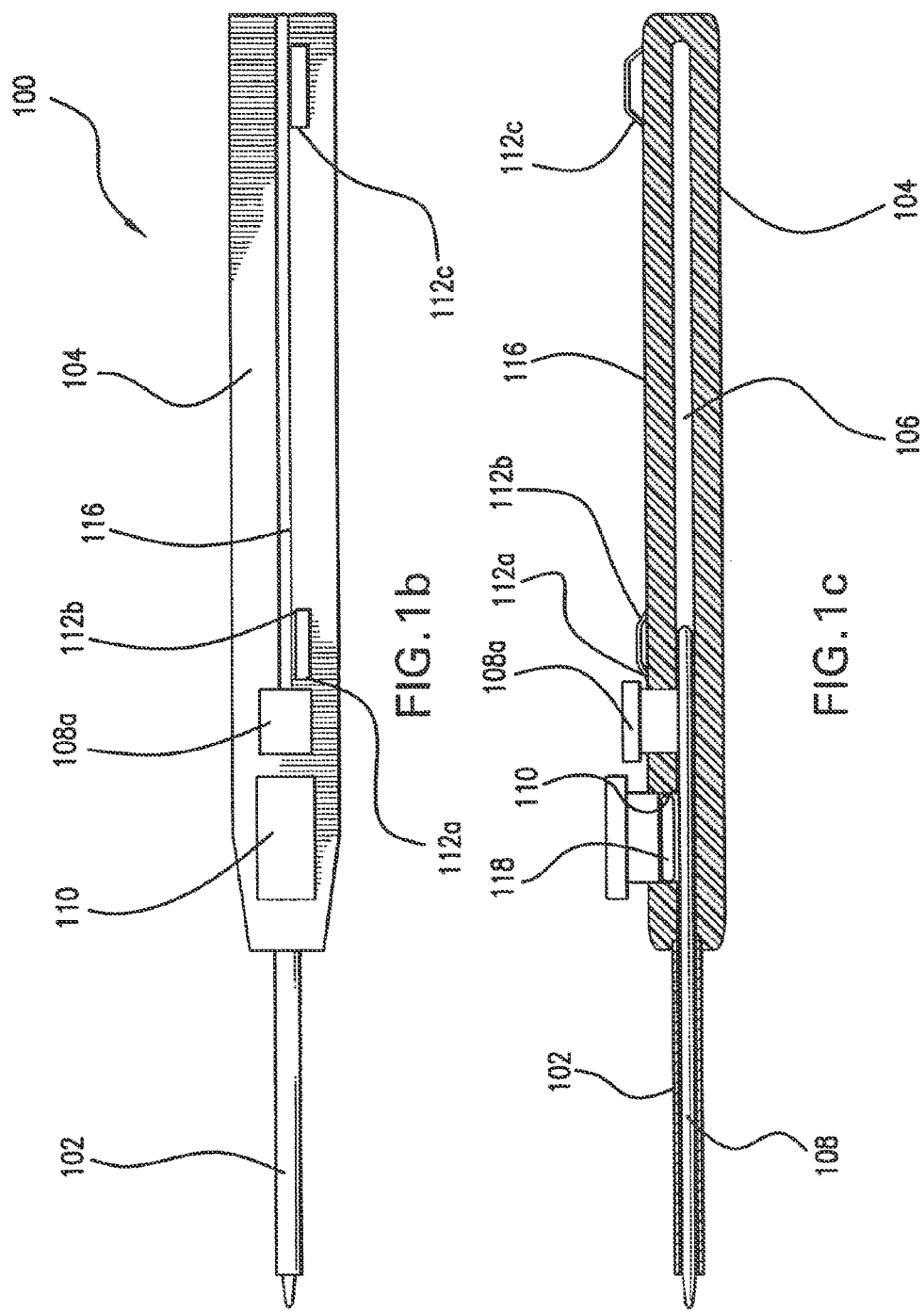

INSERTION DEVICE AND METHOD

RELATED APPLICATIONS

This application is a continuation of and claims priority to pending U.S. patent application Ser. No. 11/447,980, filed on Jun. 7, 2006 and abandoned on Dec. 19, 2012, which claims the benefit of provisional application No. 60/688,371, filed Jun. 8, 2005, each of which are incorporated herein by reference in their entirety.

BACKGROUND OF THE INVENTION

1. Field of the Invention

The present invention relates generally to the insertion of subcutaneous biosensors and, more specifically, to a device and method for implanting a biosensor at a selected site within the body of a patient.

2. Discussion of Related Art

Biosensors have been increasingly used to monitor physical characteristics of human and animal subjects. Such biosensors can be placed underneath the skin of a subject and used to measure, for example, blood glucose levels. An example of such a biosensor can be found in U.S. Pat. No. 6,330,464, the disclosure of which is incorporated herein by reference. There, an optical-based biosensor is disclosed which is capable of detecting the presence or amount of analyte in blood. Of course, such biosensors must be compatible with human and animal tissue and must maintain their integrity within moisture-rich environments. Oftentimes, the exterior of the biosensors are made of materials sensitive to the drying effects of air and must be constantly hydrated in order to maintain device integrity. For example, U.S. Pat. No. 6,330,464 discloses optical based sensors with fluorescent indicator molecules distributed throughout a matrix layer coated on the exterior surface of the sensor body. Of course, the biosensors must also be kept sterilized prior to insertion into the subject in order to avoid infection.

Certain insertion devices are known in the art for implanting sensors subcutaneously into subjects. For example, U.S. Pat. No. 4,787,384 discloses a system and device for implanting a solid identification marker underneath the animal's skin that allows scientists to mark a given animal for tracking or testing purposes. However, this system has several disadvantages. First, the system contains at least one projection extending into the hollow tube that is configured to trap the marker in place by friction fitting. Such a projection could damage the coating of a biosensor, especially in the case where the exterior surface of the biosensor is coated with an indicator chemistry and the like. Also, the disclosure of U.S. Pat. No. 4,787,384 does not teach or suggest providing for consistent hydration of the marker for the period prior to insertion. Accordingly, the disclosure provides no means of hydrating a biosensor.

Insertion devices for implanting sensors are also described in, among others, U.S. Pat. Nos. 6,936,006, 5,074,318 and 5,002,548.

What is desired, therefore, is a system and method to overcome at least some of the disadvantages of the prior art and to effectively store and insert sterilized biosensors into subjects while preserving biosensor integrity.

SUMMARY OF THE INVENTION

In one aspect, the present invention provides an insertion device having a support device including a channel that houses a slidable plunger. The plunger has an extension arm that is attached to the plunger and extends outside of the support device through a slot allowing the user to slide the plunger back and forth within the channel. In one embodiment, the user can monitor the position of the plunger by viewing the location of the extension arm relative to a plurality of ramps located on the support device.

The insertion device in accordance with one aspect of the present invention also provides a hydration storage compartment for the storage of the biosensor preferably in a sterile, hydrating environment. In one embodiment, the hydrating compartment includes a plug that resides above the biosensor which enables the biosensor to be securely maintained within the hydrating compartment. In another embodiment, the biosensor is sandwiched between the plug and plunger as it resides in the hydration storage compartment. In a preferred embodiment, the plug contains a slot that allows fluid to enter and exit the hydration storage compartment so that the biosensor is properly hydrated during storage and prior to insertion into the patient.

The insertion device according to one aspect of the invention also includes a hollow tube having dimensions that allow the plunger and biosensor to travel within the hollow tube. In one embodiment, a distal end of the hollow tube is configured such that it can be inserted into the skin of the subject. Also in accordance with this embodiment, the plunger, biosensor and hollow tube are configured such that the biosensor can be driven out of the distal end of the hollow tube by the plunger and into the desired location in the subject.

In another aspect, the present invention provides at least one method for inserting the biosensor into the subject. In the preferred method, the user places his/her thumb, for example, on the extension arm and moves the extension arm in proximity to the first ramp, which allows the biosensor to be located in the channel of the hollow tube. The user then pushes the plug down toward the channel to secure the biosensor into the channel. The user then pushes the plunger toward the distal end of the apparatus by using the extension arm to a position in proximity to the second ramp. The user then continues to push the plunger over the third ramp indicating to the user that the biosensor has exited the distal end of the hollow tube and has entered the subject.

In another aspect, the present invention provides a package assembly for storing the insertion device so that the insertion device and biosensor remain sterile and properly hydrated prior to use. In a preferred embodiment, the package assembly containing the insertion device is sealed with a sterile barrier allowing the insertion device and biosensor to be sterilized. In another embodiment, the sterile barrier contains a septum through which hydrating fluid is permitted to enter the sealed, sterilized package assembly, thereby allowing the insertion device and biosensor to be hydrated. In an additional embodiment, the package includes flaps and slotted clasps extending from the back of the package which enables the package to stand vertically. The vertical orientation of the package advantageously allows the sterile hydrating fluid to penetrate the hydration chamber and bathe the biosensor prior to use without leaking from the package cavity.

The above and other features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, help illustrate various embodiments of the present invention and, together with the description, further serve to explain the principles of the invention and to enable a person skilled in the pertinent art to make and use the invention. In the drawings, like reference numbers indicate identical or functionally similar elements.

FIG. 1b shows a top view of the insertion device of FIG. 1a.

FIG. 1c. shows a side cutaway view of the insertion device of FIG. 1a.

DETAILED DESCRIPTION OF PREFERRED EMBODIMENTS

The present invention includes an apparatus and method for implanting a biosensor (such as, for example, a biosensor for measuring the presence or amount of blood glucose levels or other analytes of interest) in a patient subject. The present invention also includes an apparatus for packaging and storing the instrument and biosensor so as to ensure hydration and sterility prior to use.

Figure 1A:
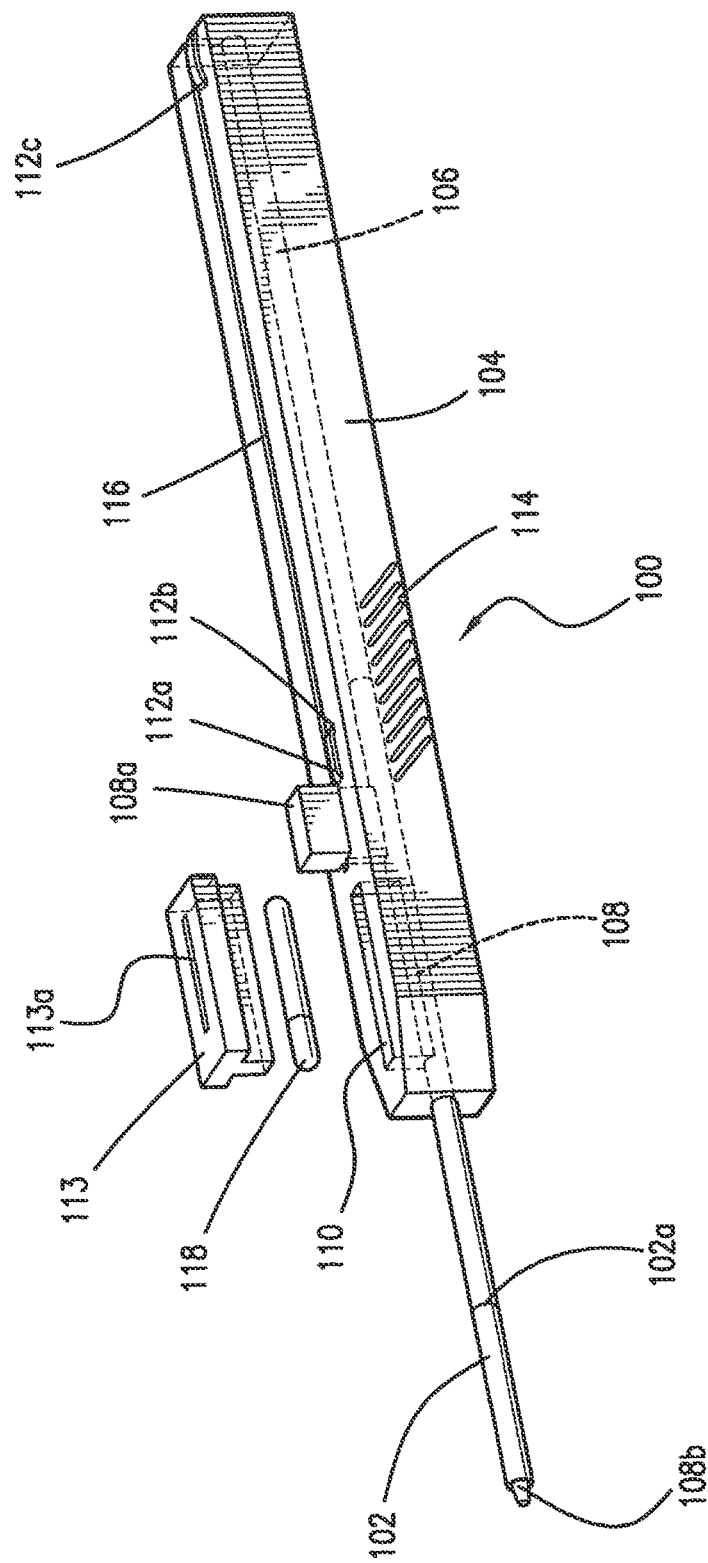
FIG. 1a shows an exploded view of the insertion device in accordance with one aspect of the present invention.

Referring to FIGS. 1a, 1b and 1c, in one embodiment of the present invention, the apparatus 100 includes a hollow tube 102 having an entrance and exit opening. The hollow tube 102 is supported by a support device 104. In a preferred embodiment, the support device 104 contains a biosensor hydration storage compartment 110 which is configured to store the biosensor 118 and hydrating solution.

A plunger or core 108 is located within the support device 104 and is configured to slide within a channel 106 in the support device 104. The channel 106 is preferably a circular channel but also may be configured to have different shapes, such as, for example, square, rectangle or triangle. The plunger 108 is also configured to slide within the hollow tube 102. The channel 106 is preferably concentric with the hollow tube 102. The plunger 108 in one embodiment has a forward and backward position relative to the support device 104. The plunger 108 may include an extension or arm 108a which allows a user of the apparatus 100 to move the plunger 108 forward and backward in the apparatus 100 along the longitudinal axis of the channel 106 and hollow tube 102. A slot 116 or the like may be provided in the support device 104 for allowing the extension 108a to move freely along the support device 104.

Figure 4:
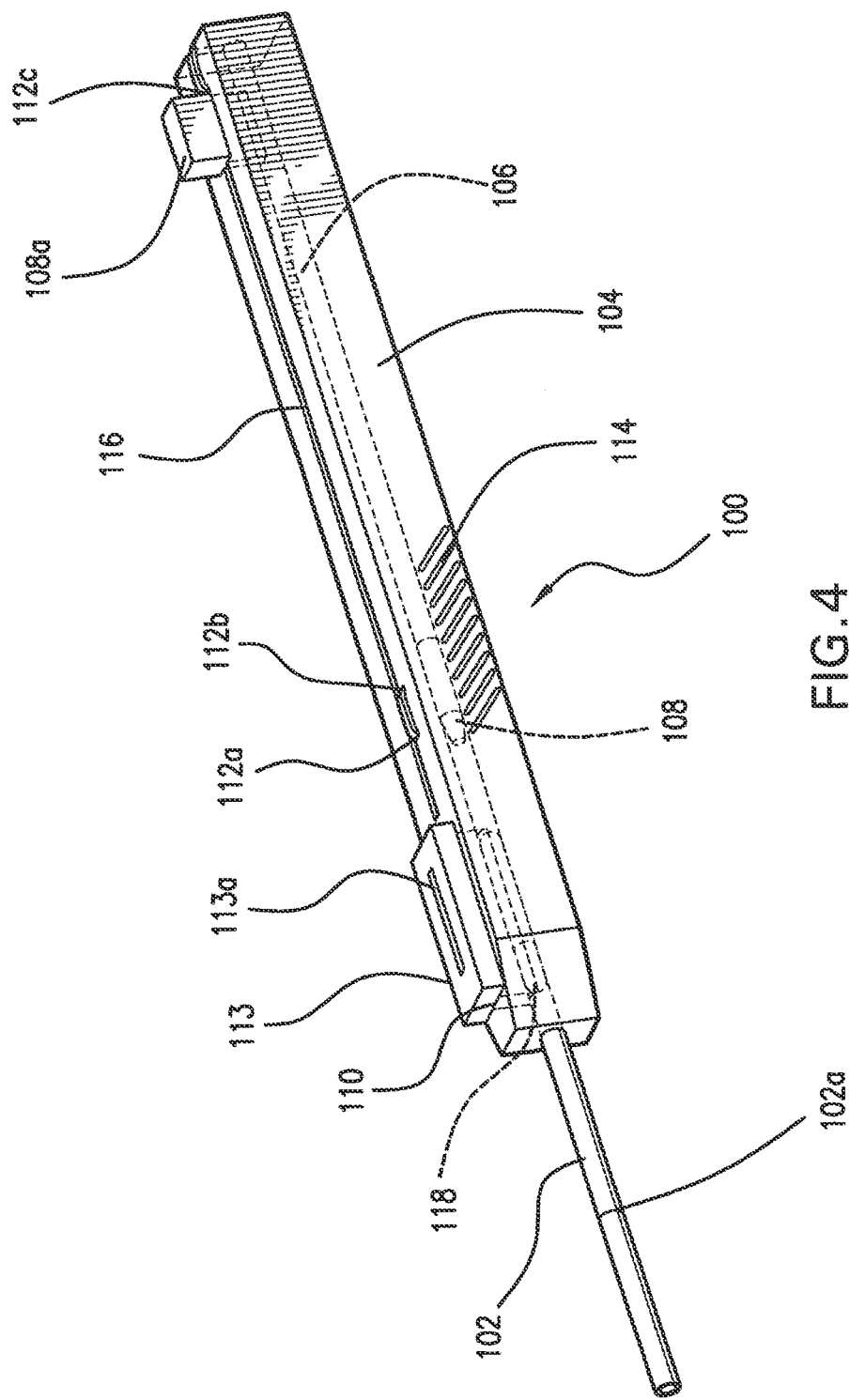
FIG. 4 shows the insertion device of FIG. 1 and illustrates the positioning of the biosensor in the channel in accordance with one aspect of the present invention.
Figure 5:
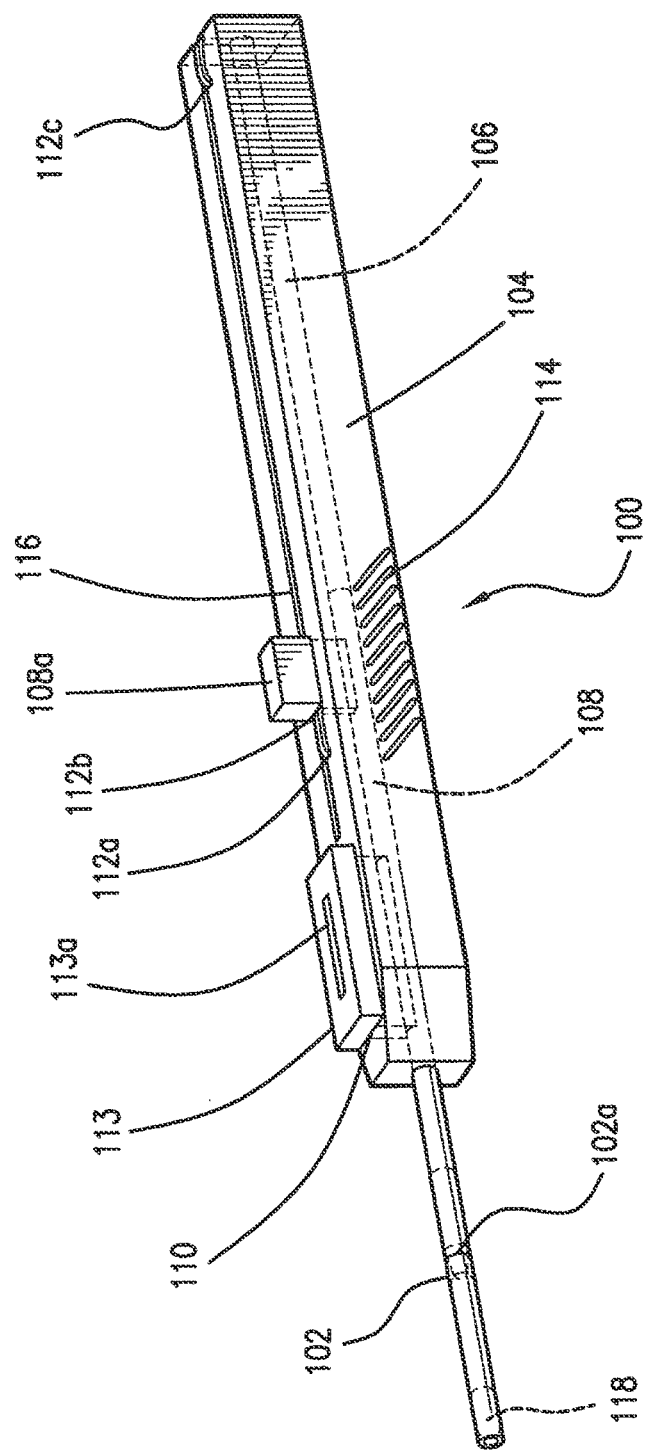
FIG. 5 shows the insertion device of FIG. 1 and illustrates the positioning of the biosensor toward the distal end of the hollow tube in accordance with one aspect of the present invention.
Figure 6:
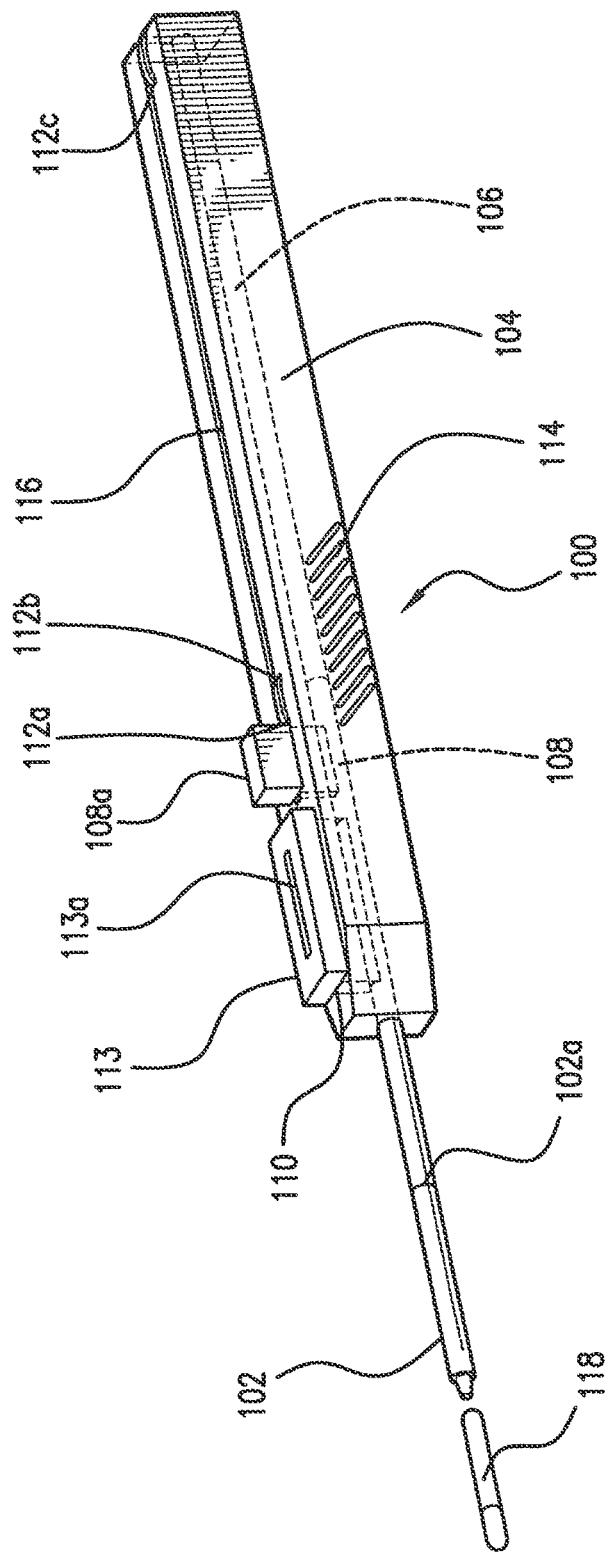
FIG. 6 shows the insertion device of FIG. 1 and illustrates the biosensor being ejected from the end of the hollow tube in accordance with one aspect of the present invention.

In one embodiment, the present invention may include one or more elements that facilitate limiting the motion of the plunger 108 and identifying the location of the plunger 108 along the channel 106 and hollow tube 102. As shown in FIGS. 1a, 1b and 1c, the present invention may include any or all of ramps 112a, 112b and 112c provided on the support device 104. The ramps 112a, 112b and 112c are configured to contact the extension arm 108a in order to limit the motion of the plunger 108 and indicate to the user the location of the biosensor 118 within the channel 106 and hollow tube 102. For example, in one embodiment, ramp 112c indicates the backward most location of the plunger 108 and, in a preferred embodiment, acts as a stop to prevent further backward movement of the plunger 108, as reflected in FIGS. 3 and 4. Ramp 112b also may be used, in accordance with one embodiment, to indicate that the biosensor is located at the distal end of the hollow tube 102, as illustrated in FIG. 5. Ramp 112a also may be used, in accordance with one embodiment, to indicate that the biosensor has been ejected from the end of the hollow tube 102 and into the patient subject, as illustrated in FIG. 6.

In accordance with a preferred embodiment, the support device 104 may include a biosensor hydration storage compartment 110 with hydration storage compartment plug 113 which is configured to be inserted into the storage compartment 110 and positioned adjacent to the channel 106. The hydration storage compartment plug 113 may have one or more slot openings 113a allowing hydration fluid to enter the hydration storage compartment 110. The plug 113 secures the biosensor 118 within the apparatus 100 hydration storage compartment 110 while the biosensor 118 is bathed in hydration fluid. In accordance with another aspect of the present invention, the hydration chamber may also receive one or more sterilization fluids, such as, for example, Cidex sterilization fluid.

In accordance with a preferred embodiment, the biosensor 118 is capable of being exposed to sterilizing gas, such as ethylene oxide (ETO) gas, while present within the apparatus 100 and hydration storage compartment 110.

The support device 104 of the present invention may be constructed of any suitable material such as, for example, an injected molded plastic. The hollow tube 102 may be constructed of a suitable, substantially rigid material such that the hollow tube may be inserted into the skin of the patient subject. In one embodiment, the hollow tube 102 is a needle or the like. In another aspect of the present invention, the hollow tube 102 has a distal end which may be beveled or tapered to facilitate insertion into the patent subject. The support device 104 also may have multiple ridges 114 positioned on the bottom surface for ergonomic feel during use.

The plunger 108 can be a guide-wire, plastic injected molded piece, stylet, or the like and preferably includes a beveled or tapered distal end 108b (See FIGS. 1a, 1b and 1c). In one embodiment, the beveled or tapered distal end of the plunger matches the beveled or tapered distal end of the hollow tube 102. This configuration may help to prevent unwanted coring of body tissue during the insertion process.

Figure 2:
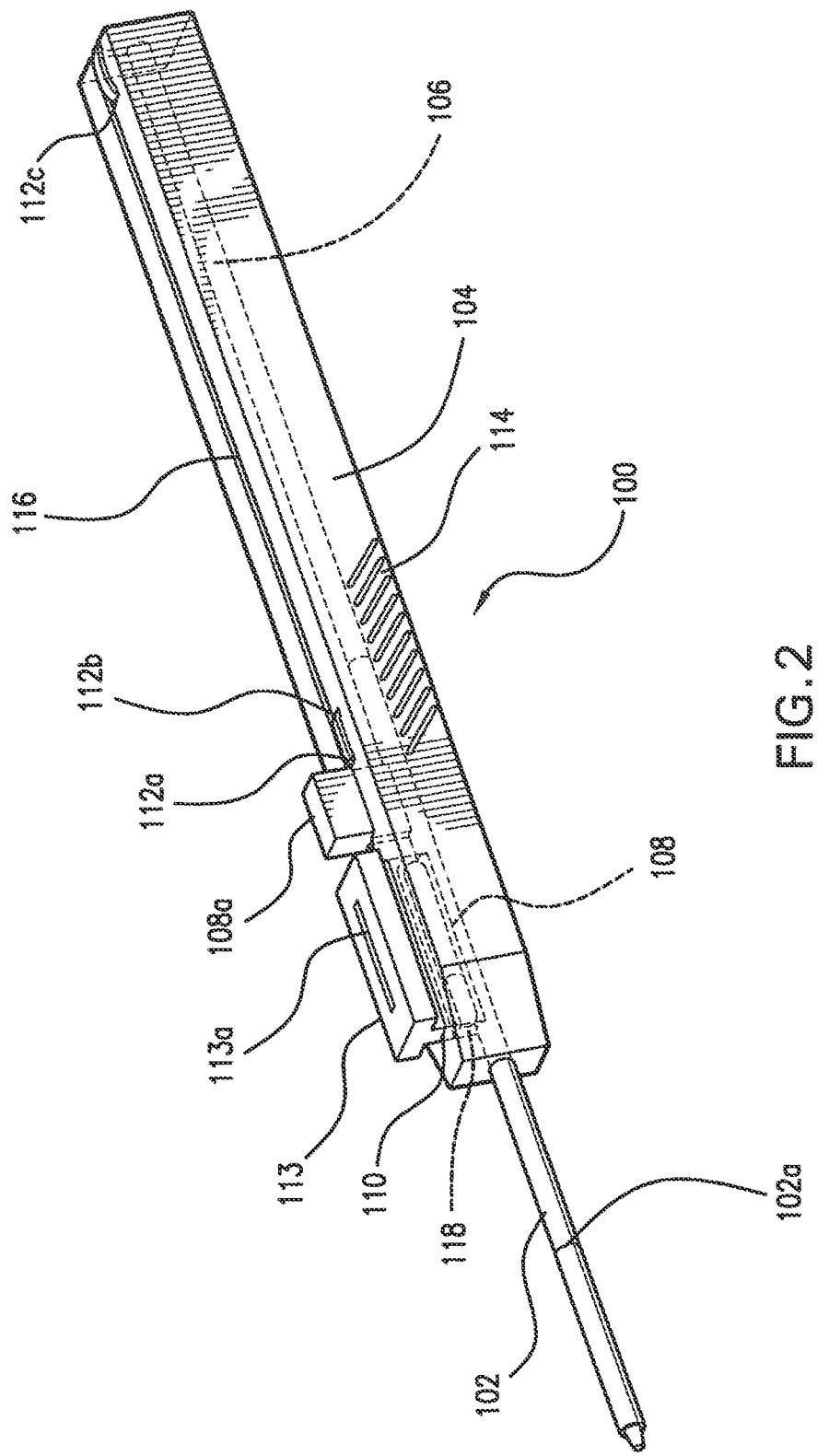
FIG. 2 shows the insertion device of FIG. 1 and illustrates the biosensor in the hydration storage compartment in accordance with one aspect of the present invention.

FIG. 2 illustrates the insertion device according to one embodiment of the present invention where the biosensor 118 is securely positioned within the hydration compartment 110 by plug 113. When the extension 108a is positioned in proximity to the third ramp 112a, the plunger 108 will serve as a "floor" for the biosensor hydration storage compartment 110, trapping the biosensor 118 in this location when the plug 113 is secured above the biosensor 118.

Figure 3:
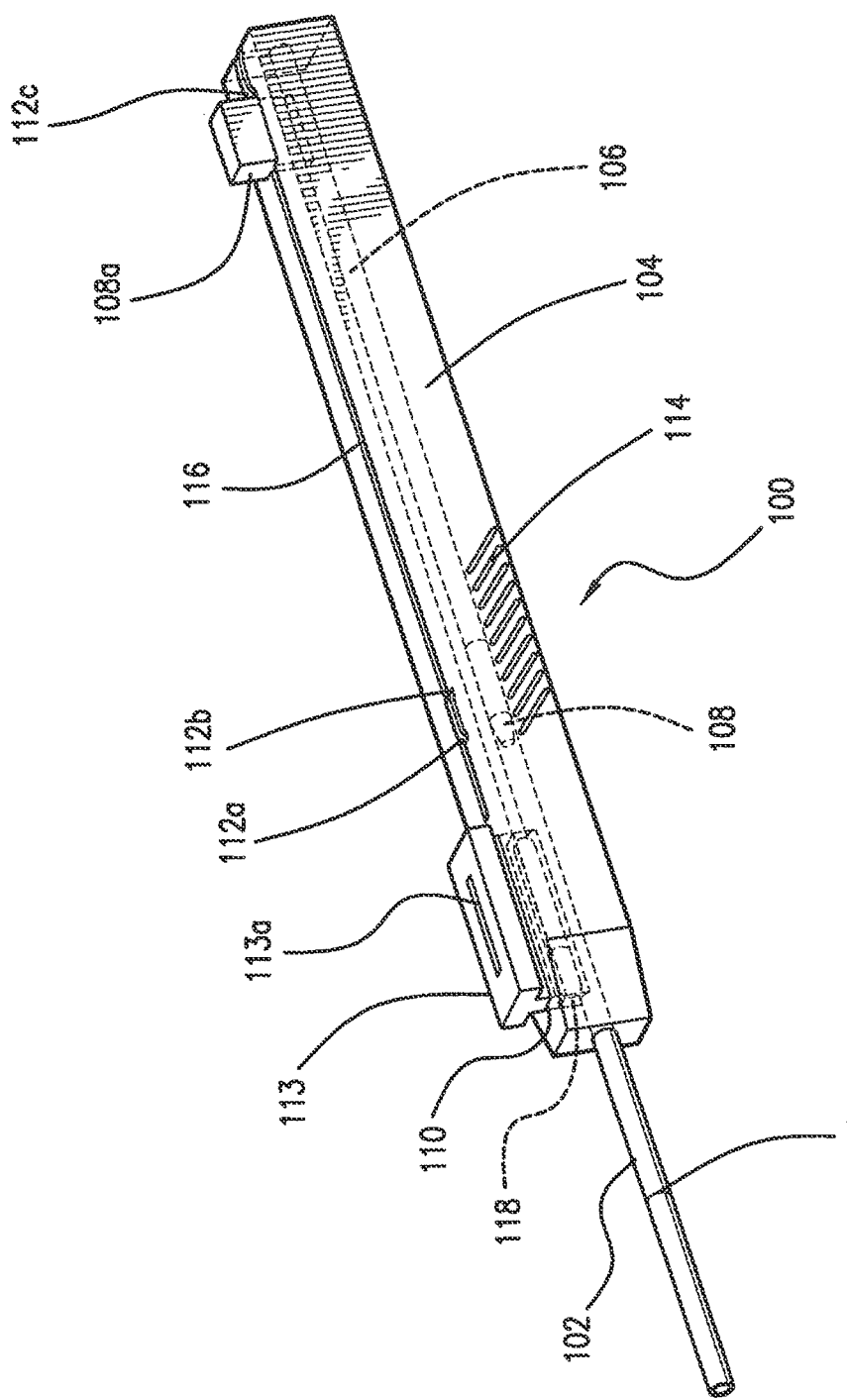
FIG. 3 shows the insertion device of FIG. 1 and illustrates plunger extension positioned such that the biosensor is permitted to move into the channel in accordance with one aspect of the present invention.

FIG. 3 illustrates the insertion device according to one embodiment of the present invention wherein the plunger extension 108a is positioned in the backward most position in proximity to first ramp 112c. The plunger may be moved to this position by the user by sliding extension 108a in proximity to the first ramp 112c. At this backward most position, the distal end of the plunger 108 moves beyond the location of the hydration storage compartment 110. In this position, the biosensor 118 no longer has the plunger 108 as a "floor" and, as a result, moves into the channel 106 in front of the distal end of plunger 108, as illustrated in FIG. 4. In one embodiment, also illustrated in FIG. 4, the hydration storage compartment plug 113 is then pushed downward, ensuring that the biosensor 118 is firmly positioned within the circular channel 106 and ready for travel along the circular channel 106 and hollow tube 102 and into the subject.

Referring to FIG. 5, the extension 108a is illustrated in an advanced position toward the second ramp 112b. In this position, the distal end of plunger/core 108 contacts the biosensor 118 and pushes the biosensor 118 through the circular channel 106 and into the hollow tube 102. When the extension 108a reaches the second ramp 112b, this alerts the user that the biosensor 118 is at the end of the hollow tube 102. At that point, the distal end of the plunger 108 is at its pre-insertion position 102a within the hollow tube 102.

FIG. 6 illustrates the insertion device according to one embodiment of the present invention wherein the plunger extension 108a positioned in the forward most position in proximity to the third ramp 112a. As the extension 108a is moved by the user from the second ramp 112b to the third ramp 112a, the plunger 108 continues its movement toward the distal end of the hollow tube 102 thereby causing the biosensor 118 to be ejected into the patient subject.

In one embodiment, as the plunger 108 moves toward the distal end of the hollow tube 102, the support device 104 will move in the opposite direction. This is accomplished, for example, when the thumb (resting on the extension 108a) and the forefinger (resting on the ridges 114) move in opposite directions. The plunger extension 108a will come in contact with the end of the slot 116 in the support device 104 that will act as a stop when moving the biosensor 118 toward the distal end of the hollow tube 102, signifying ejection of the biosensor 118. In accordance with another aspect of the present invention, the plunger 108 may be restricted from moving in the backward direction thereby ensuring the biosensor 118 is fully ejected from the apparatus 100. The tip of the hollow tube 102 is preferably then removed from the subject.

Referring back to FIG. 1a, in accordance with one embodiment, the biosensor 118 may be loaded into the hydration storage compartment 110 of the apparatus 100 with the extension 108a positioned in proximity to the third ramp 112a. When the biosensor 118 is loaded into the apparatus 100, the hydration storage compartment plug 113 traps the biosensor 118 in the hydration storage compartment 110. The plug 113 remains secured within the walls of the hydration storage compartment 110, in one embodiment, by virtue of friction fitting or other equivalent methods known in the art. In accordance with another embodiment of the present invention, the biosensor may be loaded into the hydration storage compartment 110 when the plunger extension 108a is in the back position in proximity to first ramp 112c. In this embodiment, the plug 113 is fully inserted into the hydration chamber 110 thereby securing the biosensor within the channel 106.

As described above, the ramps 112a, 112b and 112c may be provided on the surface of the support device 104 to limit the movement of the extension 108a and plunger 108 and to signal to the user the location of the plunger 108 within the channel 106. For example, the third ramp 112a may be provided toward the distal end of the support device 104 to temporarily lock the plunger/core 108 in place during loading, assembly, shipment and storage of the apparatus 100.

In the preferred embodiment, referring to FIG. 3, the first ramp 112c, may be a ribbon protruding from the surface of the support device 104, preventing the extension 108a from moving beyond the backward most position. For example, in one embodiment, the first ramp 112c may be a ribbon of material fixed into and extending from the support device 104 at the backward most position of the extension 108a and arching back toward the rear of the support device 104, as shown in FIG. 3. The first ramp 112c thereby becomes an obstacle to movement for the extension 108a and plunger 108, and also indicates to the user the location of the plunger 108 and biosensor 118. The first ramp 112c need not be a ribbon, but may be configured as any of a number of protrusions extending from the support device 104 preventing the extension 108a from moving beyond its backward most position. The protrusions can be made of any material known in the art, including, for example, plastic and/or metal. The first ramp 112c may also be a part of the support device 104, whereas a plastic mold of the support device 104 could include such a protrusion.

In one embodiment of the invention, as illustrated in FIGS. 5 and 6, the second and third ramps 112b and 112a can be created using a ribbon of material extending from the support device 104 in proximity to the distal end of the support device 104. The ribbon creating the second and third ramps 112b and 112a, in one embodiment, is configured in such a way so as to allow the extension 108a to come to a stop at the second ramp 112b, but to allow the extension to ride up the second ramp 112b, over the ribbon body, and down the third ramp 112a, temporarily securing the extension 108a and plunger 108 in a set position after the biosensor 118 has been expelled. The ribbon can be configured in such a way so as to allow the user to move the extension 108a back up the third ramp 112a, over the ribbon body, and down the second ramp 112b. The second and third ramps 112b and 112a need not be created by a ribbon, but may be any of a number of protrusions extending from the support device 104. The protrusions can be made of any material known in the art, including plastic and/or metal. The protrusions forming second and third ramps 112b and 112a may made as integral parts of the support device 104 or may be affixed to the support device 104 by known means, such as an adhesive.

In other embodiments, the ramps 112a, 112b and 112c need not be protrusions, but may be notches or the like in the support device 104, which are configured to engage the extension 108a at set positions and indicate to the user the location of the plunger 108 and biosensor 118.

The hydration storage compartment 110 is preferably sized to house only one biosensor, but the invention is not meant to be limited to such an embodiment. In alternative embodiments (not shown), the hydration storage compartment 110 may be constructed to hold multiple biosensors. In still other embodiments, the support device 104 may be configured to have multiple hydration storage compartments 110 along the surface of support device 104.

The hydration storage compartment 110 can be fabricated from a porous material or include holes to allow liquid to pass into the chamber from the outside, such as through slot 113a in plug 113. In one embodiment, it is intended that the biosensor 118 be placed within the hydration storage compartment 110 of the apparatus 100 prior to packaging, as illustrated in FIG. 2. In this embodiment, it is desired that the biosensor 118 be treated, hydrated, sterilized or the like, after the biosensor 118 is inserted into the hydration storage compartment 110. Therefore, any number of hydration methods known in the art can be used to ensure that fluid enters the hydration storage compartment 110.

Figure 9A:
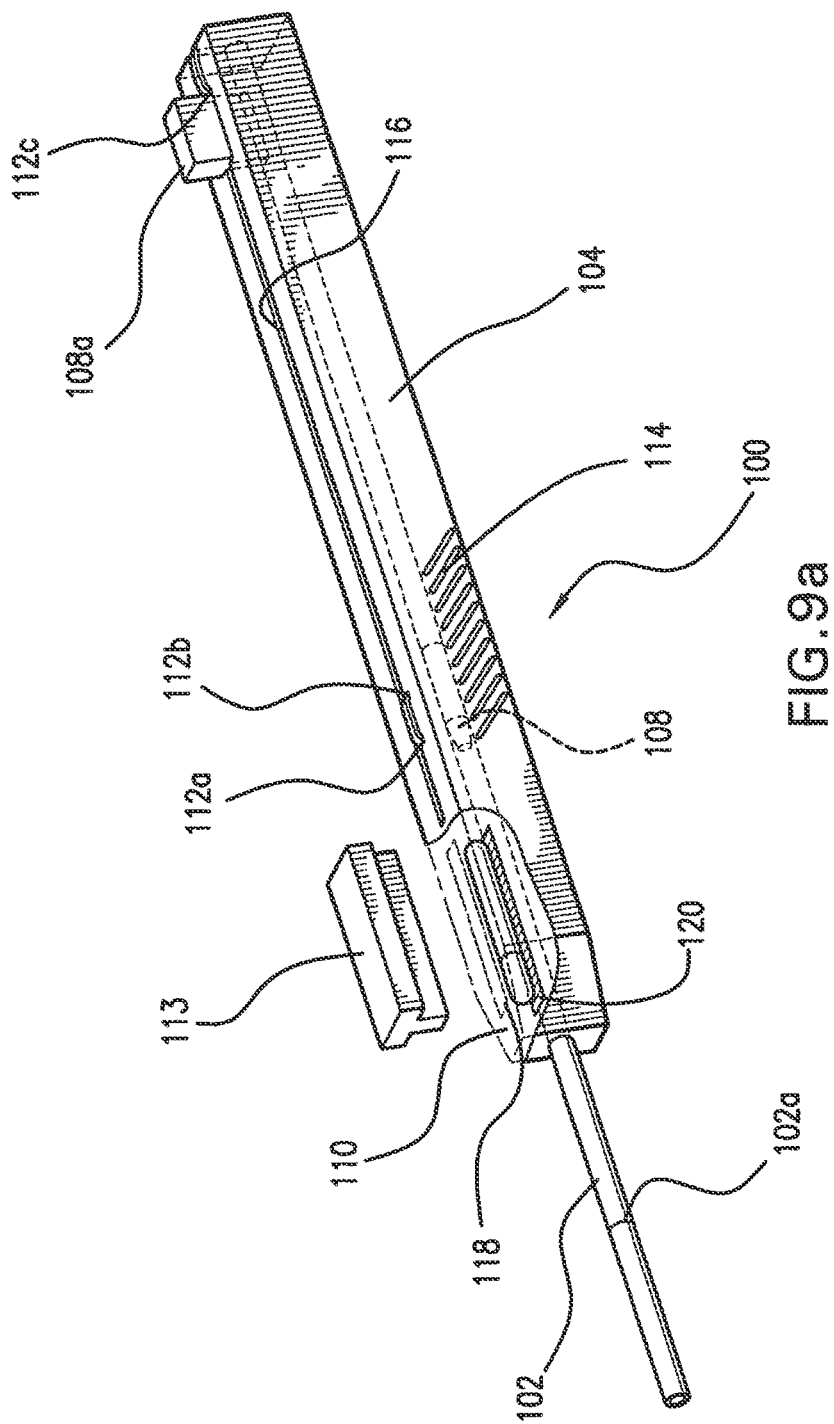
FIGS. 9a and 9b show the hydration chamber of the insertion device having a breakable floor in accordance with another embodiment of the present invention.
Figure 9B:
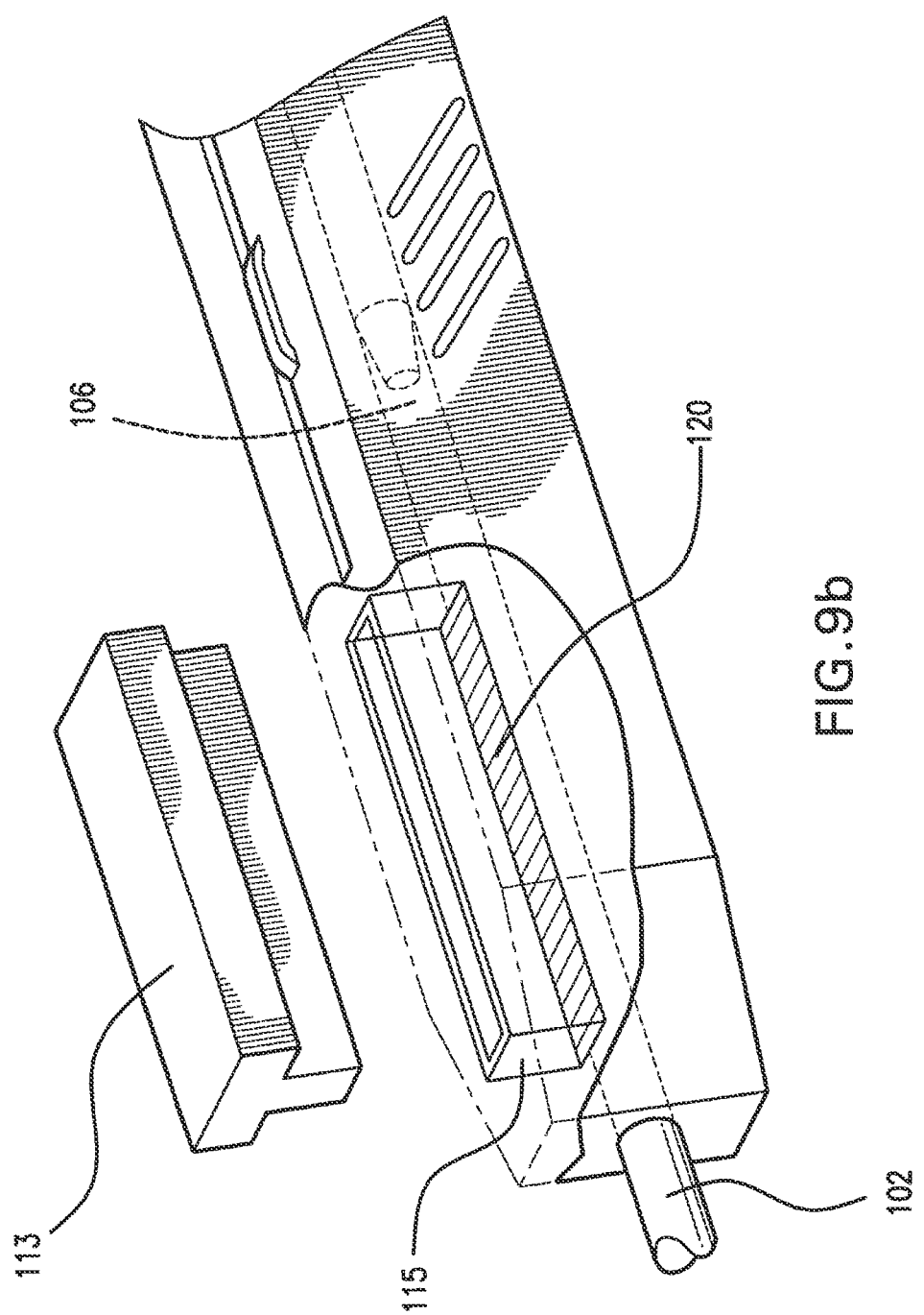

In another embodiment of the present invention, referring to FIGS. 9a and 9b, the hydration storage compartment 110 contains hydrating fluid and a breakable floor 120. In this embodiment, the breakable floor 120 prevents the biosensor 118 and fluid from entering the channel 106 prior to use of the device. In this embodiment, the hydration storage compartment 110 is defined by the walls of the device 115, the breakable floor 120, and the plug 113. The plug 113, in one embodiment, is non-porous and creates a fluid-tight seal within the compartment 110, thereby preventing the fluid from leaking outside the compartment 110. In this embodiment, the user moves the plunger extension 108a back to the first ramp 112c and applies pressure to the plug 113 so that the biosensor 118 breaks through the breakable floor 120 and enters the channel 106 along with the hydrating fluid. The breakable floor 120 can be made of any number of materials known in the art that can hold fluid and break open upon suitable pressure without fragmenting, such as aluminum foil, rubber and/or plastic.

Figure 10A:
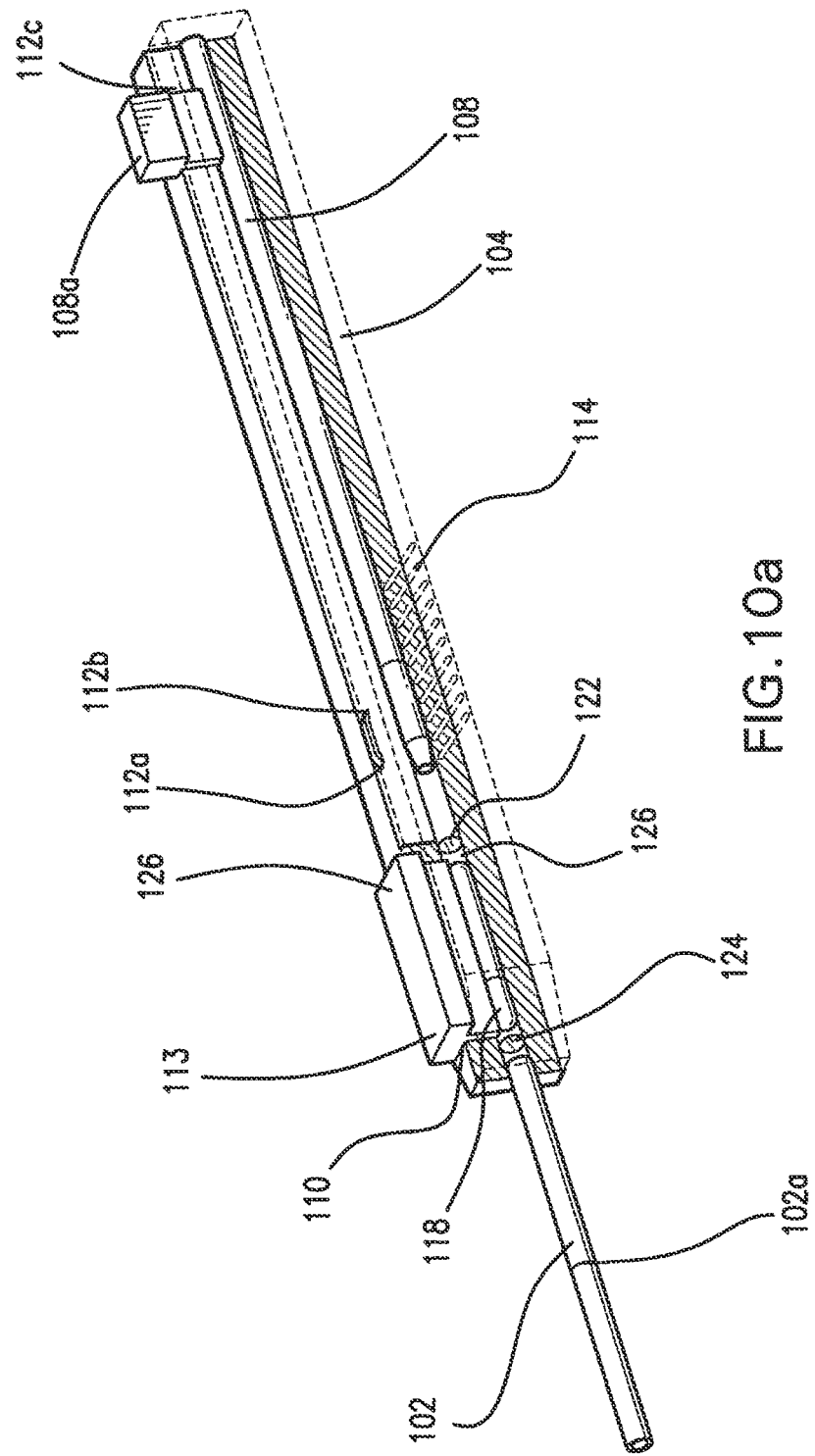
FIGS. 10a and 10b show the channel of the insertion device having first and second breakable barriers in accordance with another embodiment of the present invention.
Figure 10B:
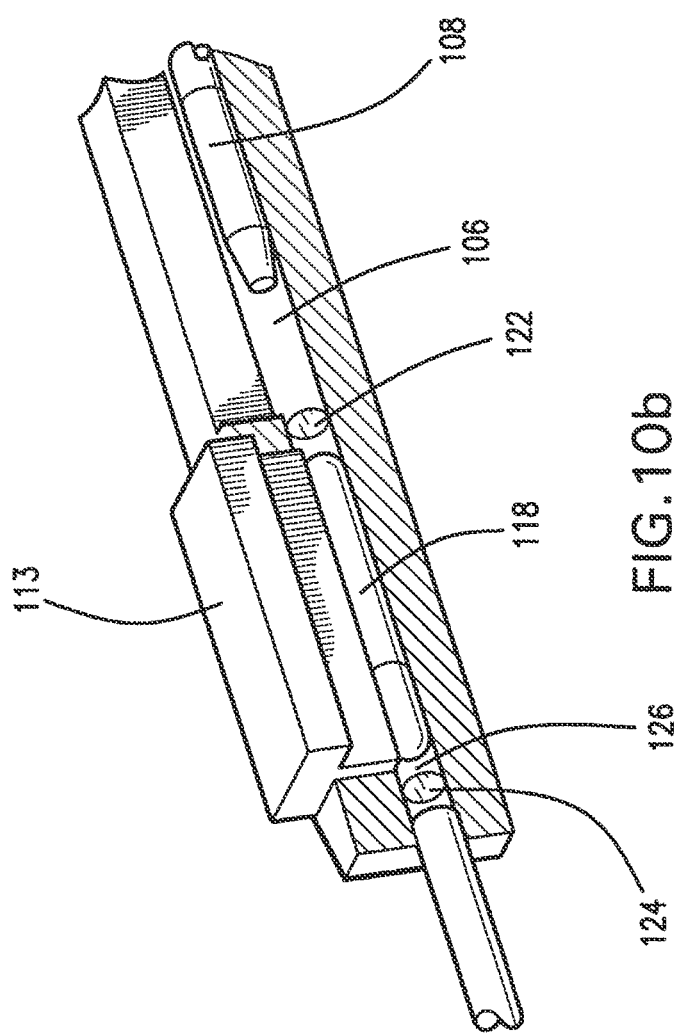

In another embodiment of the present invention, referring to FIGS. 10a and 10b, the biosensor 118 and fluid are placed within a hydration chamber 126 which is defined by the channel 106 at a bottom end, side walls including a first breakable barrier 122 and a second breakable barrier 124 located within the channel 106, and the plug 113 at the top. The plug 113 secures the biosensor and seals the fluid within the channel 106 prior to insertion. In this embodiment, the plunger extension 108a begins at the position located at the first ramp 112c and, when moved forward, the distal end of the plunger 108 pierces the first breakable barrier 122, and forces the biosensor 118 to break through the second breakable barrier 124 as the biosensor 118 travels down the hollow tube 102 and into the subject. This occurs while the plunger extension 108a moves past the second ramp 112b to the third ramp 112a. In this embodiment, the biosensor 118 and fluid can be loaded into the channel 106, with the plug 113 acting as the roof of this hydration chamber 126, securing the biosensor 118 and preventing the fluid from escaping the chamber 126 prior to use. The breakable barriers can be made of any number of materials known in the art that can hold fluid and break open upon suitable pressure without fragmenting, such as aluminum foil, rubber and/or plastic.

Figure 11:
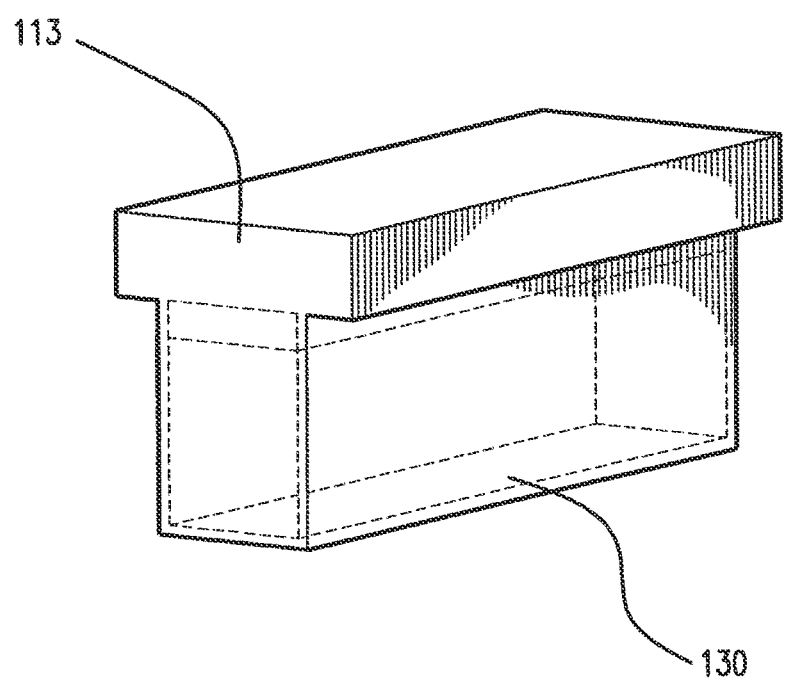
FIG. 11 shows the plug of the insertion device as being hollow and having a breakable bottom in accordance with another embodiment of the present invention.

In another embodiment, as shown in FIG. 11, the plug 113 can be configured to have a hollow chamber for containing the hydration fluid. In this embodiment, the plug 113 may be designed in such a way as to have a breakable bottom 130 so that fluid can be released to hydrate the biosensor 118 when the user applies pressure to the plug. That is, in various configurations, the plug 113 can rest atop the biosensor 118 before use. When the user applies pressure to the plug 113, the floor 130 of the plug 113 bursts open, releasing the fluid stored within the plug 113, bathing the biosensor 118 with hydrating fluid in the process. Accordingly, the breakable floor 130 can be made of any number of materials known in the art that can hold fluid and break open upon suitable pressure without fragmenting, such as aluminum foil, rubber and/or plastic. The plug 113 in accordance with this embodiment can be used in conjunction with the apparatus 100 in accordance with any of the embodiments discussed above.

Figure 8:
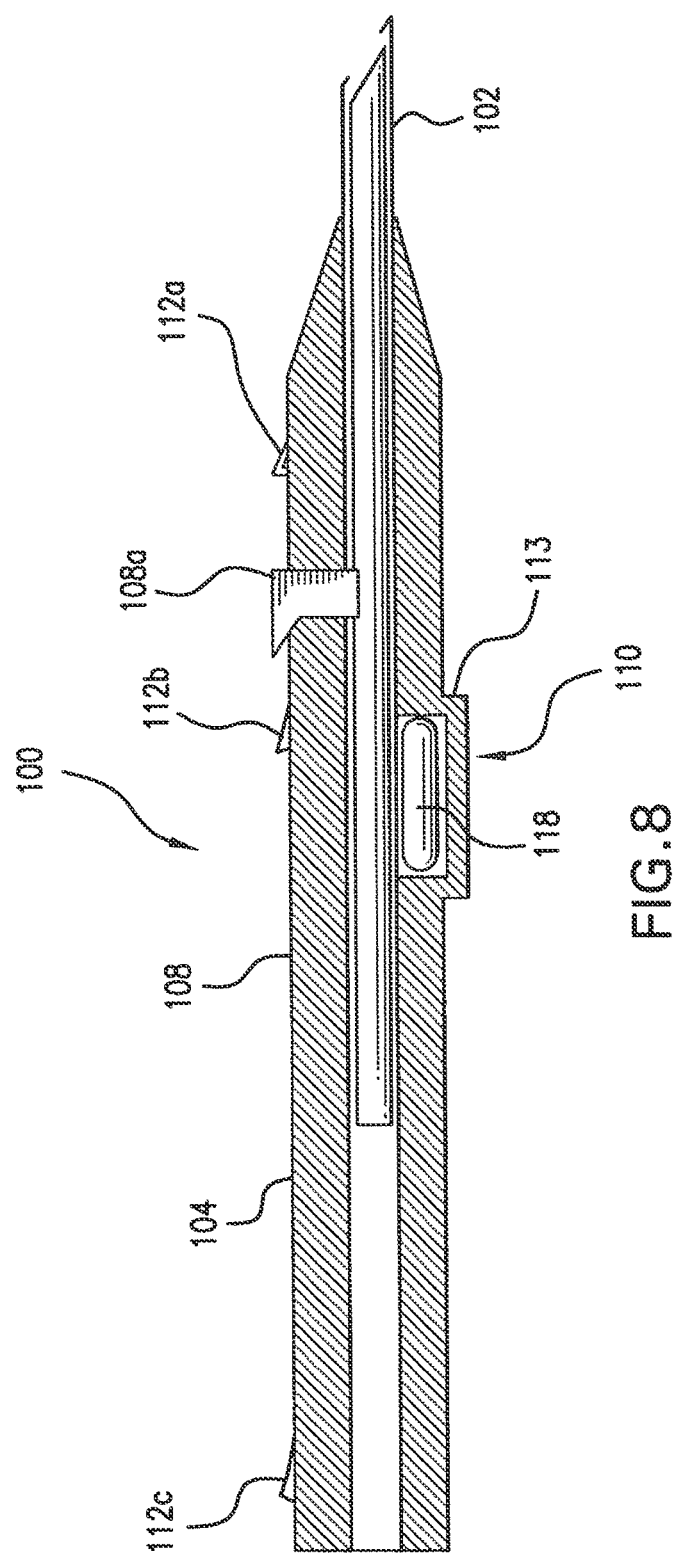
FIG. 8 shows a side cutaway view of an insertion device in accordance with another embodiment of the present invention.

Referring to FIG. 8, in another embodiment, the biosensor 118 can be loaded into the hydration storage compartment 110 located on the underside of the apparatus 100 opposite the extension arm 108a. This can be accomplished, for example, with a plug 113 designed to cradle the biosensor 118. In other words, for any and all embodiments, the plug can be designed in a multitude of ways depending on the needs that arise from the configuration and location of the storage compartment 110 on the apparatus 100. In this embodiment, it would be desirable to have the plug 113 shaped to cradle the biosensor 118 for easy loading of the biosensor 118 from the underside of the apparatus 100, thereby lowering the risk of having the biosensor 118 fall to the floor during biosensor 118 loading. In an alternative embodiment for loading the biosensor into the apparatus 100, the apparatus 100 can be flipped so that the storage compartment 110 is on top and the user can load the biosensor 118 into the compartment 110 and secure the biosensor 118 with the plug 113. The user can then flip the apparatus 100 back so that the storage compartment 110 is on the bottom, and ready for the insertion process to take place.

In this arrangement, the plunger 108 would serve as a "lid" to the hydration storage compartment 110 as opposed to a "floor" as described in other embodiments. Here, the plug 113 would serve as the "floor", thereby trapping the biosensor 118 in the hydration storage compartment 110. Similar to the other embodiments described above, once the distal end of the plunger 108 passes the hydration storage compartment 110 when extension 108a is located in proximity to the first ramp 112c, the biosensor 118 no longer has a restriction to entering into the channel 106 and in front of the distal end of plunger 108. Once in this position, the apparatus 100 can be rotated sufficiently (i.e. flipped so that the hydration storage compartment 110 is on top of the apparatus 100) to allow the biosensor to fall into the circular channel 106 by gravity. The plug 113 could then be pushed toward the channel 106 to secure the biosensor 118 into the channel 106.

Also referring to FIG. 8, the biosensor can be loaded into the apparatus 100 from either end. In one embodiment, the biosensor 118 can be loaded into the distal end of the hollow tube 102 when the extension 108a is in proximity to the second ramp 112b. The apparatus 100 can then be turned vertically so that once the biosensor 118 is inserted into the hollow tube 102 gravity causes the biosensor 118 to rest against the distal end of plunger 108 when within the tube 106. The extension 108a can then be moved backward to the first ramp 112c, indicating to the user that the biosensor is in proximity to the hydration storage compartment 110. The user can then lower the apparatus 100 horizontally so that the biosensor 118 can fall by gravity into the hydration storage compartment 110 which resides in a position such that it is at the bottom of the apparatus 100 (as shown in FIG. 8). The extension 108a can then be moved to the third ramp 112a prior to insertion, securing the biosensor 118 between the plunger 108 and plug 113. The biosensor 118 can be hydrated in a substantially similar way as described above including pores or slot openings in the support device 104, plug 113 or chamber 110.

Figure 7A:
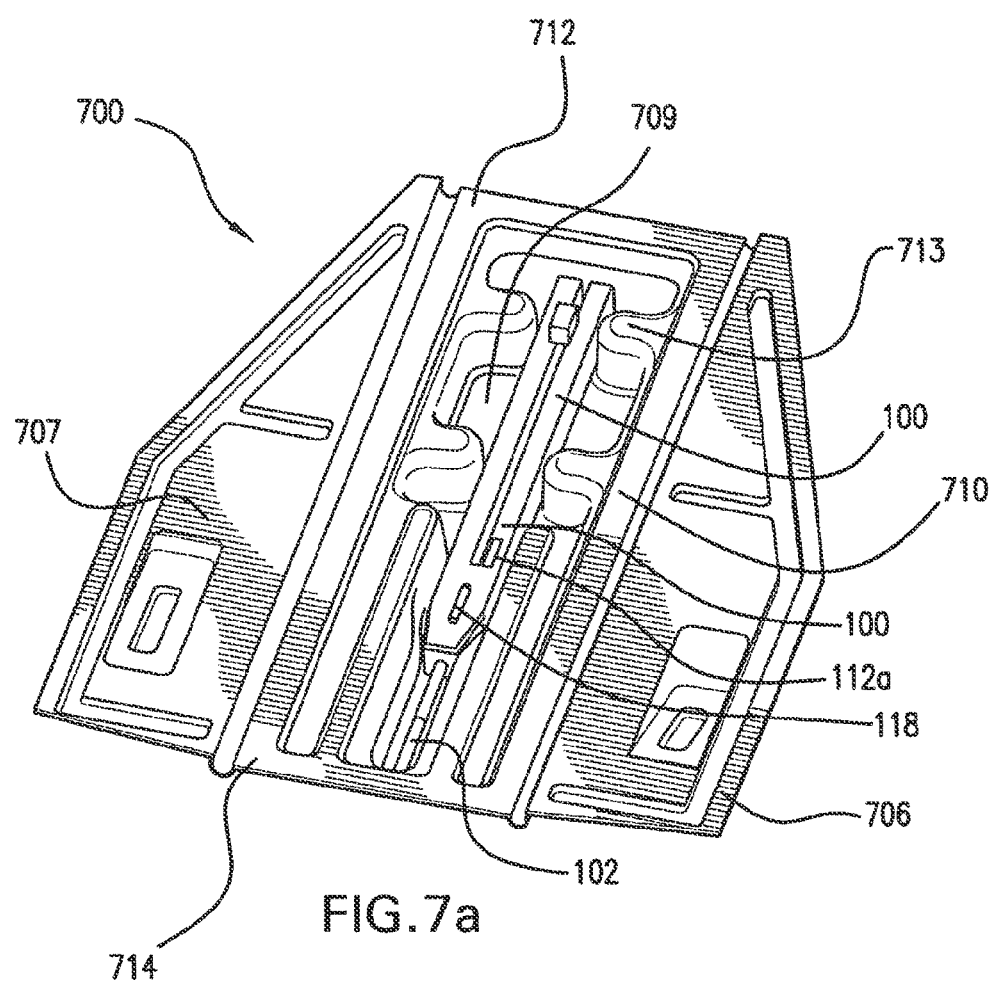
FIG. 7a illustrates a front view of a sterile package assembly for storing an insertion device in accordance with another aspect of the present invention.

In accordance with another aspect of the present invention, referring to FIGS. 7a-7e, a package assembly is provided for storing the insertion device. FIG. 7a illustrates a package assembly 700 according to one embodiment in an unfolded and loaded configuration. In particular, the package assembly 700 includes a package assembly body 714 that has an apparatus cavity 709 configured to hold the apparatus 100 containing the biosensor 118 in the hydration storage compartment 110. The cavity 709, in a preferred embodiment, is also configured to hold a sufficient volume of fluid so that the fluid can enter the hydration storage compartment 110 and bathe the biosensor 118, as illustrated in FIG. 7a. Typically, the volume of fluid necessary to bathe the biosensor 118 will be enough to fill the cavity surrounding the distal end of the hollow tube 102 and up to the location of the third ramp 112a when the device is in the package 700 and the package 700 is standing in an upright position (as described below).

In one embodiment, the package assembly body 714 is shaped to secure the apparatus 100 so that the apparatus 100 remains substantially in place even if the package is otherwise moved. The apparatus 100 may be secured in the package assembly body 714 in any number of ways, including a friction fit mold. For example, as shown in FIG. 7a, the package assembly body 714 is fashioned to conform to the shape of the apparatus 100, allowing the apparatus 100 to remain secure within the package assembly 700. In one embodiment, engagement elements 713 frictionally engage the apparatus to secure it in place. The package assembly 700 can be made of any suitable material known in the packaging arts, such as plastic including, for example, thermoform plastic.

Figure 7B:
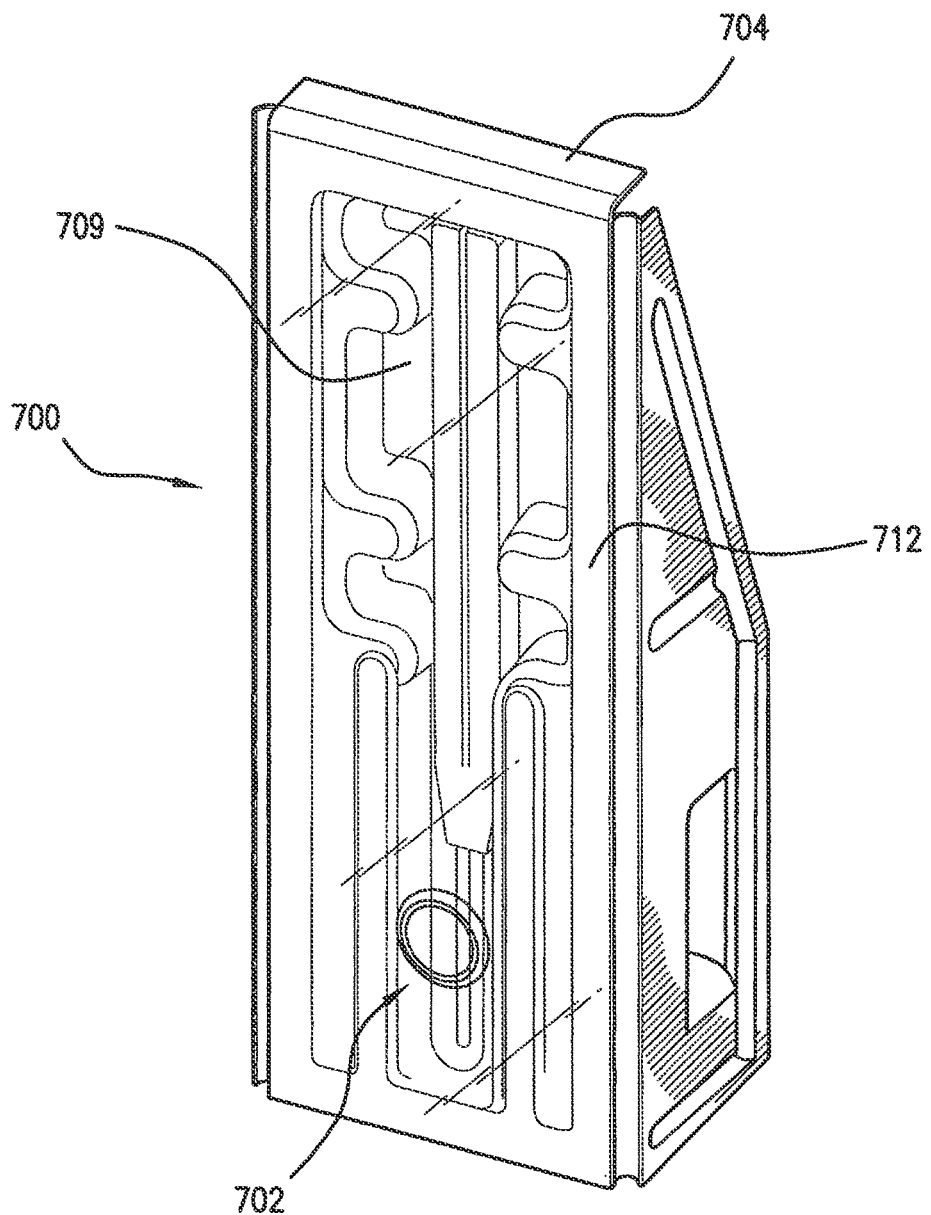
FIG. 7b illustrates a front view of a sterile package assembly for storing an insertion device with a sterile barrier layer and septum in accordance with another aspect of the present invention.

Referring to FIG. 7b, the package assembly 700 containing the apparatus 100 is sealed with a sterile barrier 704 to maintain the sterility of the apparatus and the biosensor 118. The sterile barrier 704 can be made of any suitable material, such as, for example, woven plastic (such as Tyvek®), paper or aluminum foil. In accordance with a preferred embodiment of the invention, the sterile barrier 704 is provided with a septum 702 which allows the cavity 709 to be filled with hydration and/or sterilization fluid while maintaining the sterility of the package and sterile barrier 704. In one embodiment, saline is injected through the septum 702 with, for example, a syringe. This allows the biosensor 118 to be hydrated while maintaining sterility within the package 700. The sterile barrier 704 is preferably attached to the face 712 of the package body 714 in such a way so as to create a fluid-tight seal around the outer edge of the face 712 of the package body 714. This can be accomplished with any number of glues or sealants known to persons skilled in the art.

Any number of hydration fluids can be used, such as, for example, one or more of the following: (1) inorganic salts such as sodium chloride, potassium chloride, calcium chloride, or magnesium chloride; (2) buffer salts such as phosphate, HEPES, carbonate, and citrate; (3) preservatives such as EDTA; (4) antimicrobial agents such as sodium azide, sulfites, and benzoates; (5) antibiotics, anti-inflammatory drugs and other pharmacological compounds; (6) ionic and nonionic surfactants; (7) thickening agents that can be used to increase the viscosity of aqueous solutions such as glycerol, polyethylene glycols, gelatin, agar and pectin; (8) antioxidants such as BHT, BHA; (9) vitamins such as C and E, flavonoids; and (10) Saccharides such as glucose, fructose, and sucrose. This list should not be construed to be exhaustive, but is meant to illustrate the vast array of fluids that could be used to hydrate the biosensor.

Figure 7C:
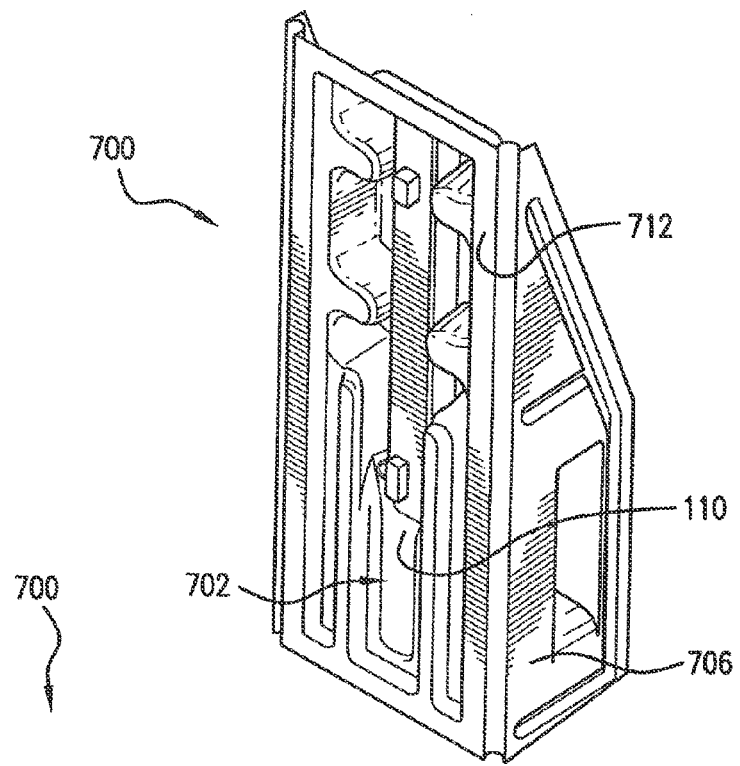
FIG. 7c illustrates a side view of the sterile package assembly for storing an insertion device in accordance with another aspect of the present invention.

In accordance with another aspect of the present invention, the package 700 is designed to store the apparatus 100 in such a way so as to allow constant hydration of the biosensor 118 while the biosensor 118 is contained within the hydration storage compartment 110. In one embodiment, as illustrated in FIG. 7c, the package 700 stands vertically, allowing the sterile fluid to penetrate the hydration chamber 110 and bathe the biosensor 118. Fluid may penetrate the hydration chamber 110 in any number of ways, including pores or slot openings in the support device 104, plug 113 or chamber 110, as described above.

Figure 7D:
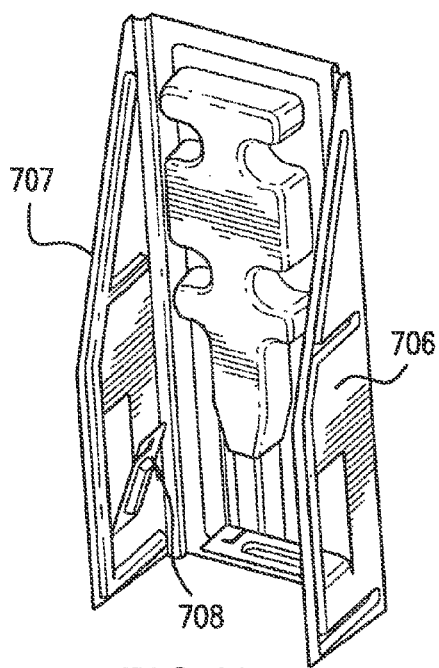
FIG. 7d illustrates a rear view of the sterile package assembly for storing an insertion device in accordance with another aspect of the present invention.
Figure 7E:
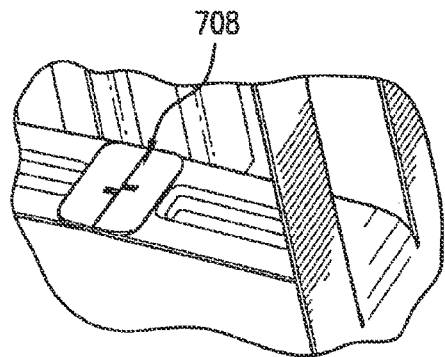
FIG. 7e illustrates a clasp assembly of the sterile package assembly for storing an insertion device in accordance with another aspect of the present invention.

In one embodiment, the package assembly 700 is configured in a vertical orientation by providing side walls 706 and 707 attached to the package assembly body 714. Side walls 706 and 707 are shown in FIG. 7a in a flat, unfolded configuration. Referring to FIGS. 7b-d, the side walls 706 and 707 are shown in a folded configuration. Referring to FIG. 7d, in order to allow the sterile package 700 to remain standing in accordance with one embodiment, package flaps 706 are folded away from the plane created by the face 712 of the package assembly 700 and sterile barrier 704. The flaps 706 are folded so as to connect with one another via slotted clasps 708, as illustrated in FIGS. 7d and 7e. This allows the package 700 to stand vertically thereby ensuring that the sterilization fluid collects in the cavity 709 so as to engulf the hydration storage compartment 110 of the apparatus 100 and thereby bathe the biosensor 118 prior to insertion into the subject.

While slotted clasps are illustrated as being formed from portions of the side walls 706 and 707, the side walls can be secured by other means. For example, the package assembly can be provided with one or more back walls or clasps attached, for example, to one or both of side walls 706 and 707. In another embodiment, clasps are not formed from the side wall material but are, instead, attached to the side walls in any known manner, such as an adhesive.

Preferably, the apparatus 100, package 700, barrier 704, septum 702 and other relevant parts are manufactured of such materials that allow them to be readily disinfected and/or sterilize by conventional means.

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:
1. A method for inserting a biosensor into a subject comprising the steps of:
  positioning at least one biosensor in a hydration compartment of a biosensor insertion instrument, the instrument comprising a support device having a continuous structure with a first end and a second end, said support device containing at least one channel enclosed within said continuous structure such as said at least one channel opens only at said first end, a plunger slidable within said at least one channel, a plug configured to secure said at least one biosensor within said hydration compartment while said at least one biosensor is bathed in hydration fluid, and a hollow tube attached to and extending from said first end of said support device, wherein the plunger serves as a floor for the compartment;
  trapping said at least one biosensor in said hydration compartment between the plunger and the plug, wherein said hydration compartment is capable of containing hydration fluid for hydrating said at least one biosensor;

moving said plunger to a first position of said support device such that the plunger no longer serves as a floor for the compartment and a biosensor is allowed to enter said channel of said support device;

pushing said plug into said compartment to secure said biosensor within said at least one channel of said support device;

moving said plunger toward a second position of said support device such that said biosensor travels through said hollow tube and is about to enter said subject;

moving said plunger to a third position of said support device such that said biosensor exits said hollow tube and enters said subject.

2. The method of claim 1, wherein said biosensor is initially located within said compartment.

3. The method of claim 1, wherein said biosensor enters said channel by gravity.

4. The method of claim 1, wherein ramps lock said plunger at said positions.

* * * * *